(12) United States Patent
Fürst et al.

(10) Patent No.: US 9,144,145 B2
(45) Date of Patent: Sep. 22, 2015

(54) C-ARM X-RAY DEVICE WITH A C-ARM AND ASSOCIATED METHOD

(71) Applicants: Jens Fürst, Herzogenaurach (DE); Norbert Herrmann, Ebnath (DE)

(72) Inventors: Jens Fürst, Herzogenaurach (DE); Norbert Herrmann, Ebnath (DE)

(73) Assignee: Siemens Aktiengesellschaft, München (DE)

( * ) Notice: Subject to any disclaimer, the term of this patent is extended or adjusted under 35 U.S.C. 154(b) by 225 days.

(21) Appl. No.: 13/960,788

(22) Filed: Aug. 6, 2013

(65) Prior Publication Data
US 2014/0044241 A1 Feb. 13, 2014

(30) Foreign Application Priority Data
Aug. 7, 2012 (DE) .......................... 10 2012 214 016

(51) Int. Cl.
*H05G 1/02* (2006.01)
*A61B 6/00* (2006.01)

(52) U.S. Cl.
CPC .. *H05G 1/02* (2013.01); *A61B 6/00* (2013.01); *A61B 6/4405* (2013.01); *A61B 6/4441* (2013.01); *A61B 6/4452* (2013.01)

(58) Field of Classification Search
CPC ............................. A61B 6/4441; A61B 6/4464
See application file for complete search history.

(56) References Cited

U.S. PATENT DOCUMENTS

| | | | |
|---|---|---|---|
| 5,050,204 A * | 9/1991 | Siczek et al. .................. 378/197 |
| 6,480,571 B1 | 11/2002 | Andrews | |
| 7,534,037 B2 | 5/2009 | Curtis | |
| 7,648,008 B2 | 1/2010 | Ohtsuka | |
| 2005/0179878 A1 | 8/2005 | Ohtsuka | |
| 2011/0200176 A1* | 8/2011 | Sharpless ..................... 378/197 |
| 2013/0129036 A1* | 5/2013 | Baumann et al. ................ 378/4 |

FOREIGN PATENT DOCUMENTS

| | | |
|---|---|---|
| DE | 60131278 T2 | 2/2008 |
| DE | 102011075979 | 11/2012 |
| JP | 2005-027914 | 2/2005 |

OTHER PUBLICATIONS

German Office Action dated Apr. 16, 2013 for corresponding German Patent Application No. DE 10 2012 214 016.6 with English translation.

* cited by examiner

Primary Examiner — Hoon Song
(74) Attorney, Agent, or Firm — Lempia Summerfield Katz LLC

(57) ABSTRACT

A C-arm x-ray device includes a C-arm and an x-ray source and an x-ray detector arranged on the C-arm. At least one damping element with an oscillation-damping effect is arranged between the x-ray source and the C-arm. Transmission of oscillations of the x-ray source onto the C-arm may be reduced with the at least one damping element. The C-arm x-ray device also includes at least one holding element arranged on the C-arm. The oscillation-damping effect of the at least one damping element may be influenced.

16 Claims, 3 Drawing Sheets

C-ARM X-RAY DEVICE WITH A C-ARM AND ASSOCIATED METHOD

This application claims the benefit of DE 10 2012 214 016.6, filed on Aug. 7, 2012, which is hereby incorporated by reference.

BACKGROUND

The present embodiments relate to a C-arm x-ray device having a C-arm and an x-ray source and an x-ray detector arranged on the C-arm.

The problem with x-ray imaging technology is that when x-ray images are produced using a C-arm x-ray device including an x-ray source arranged at one end of the C-arm, vibrations are generated. The vibrations are transmitted via the C-arm to an x-ray detector arranged at the other end of the C-arm. The vibrations develop on account of a high rotational speed of a rotary anode arranged in the x-ray source. The vibrations transmitted to the x-ray detector via the C-arm cause the x-ray detector to continuously move to and fro and thus to deflect from a basic position. X-ray images produced during such vibration phases are characterized by a poor image quality.

When x-ray image sequences are imaged (e.g., a number of x-ray images in temporal sequence) such as is implemented, for example, in angiography typically with a sequence length of 10 seconds and a frequency of 15 to 30 images per second, the vibrations also result in the entire sequence of the x-ray image sequence being negatively affected. The x-ray image sequence appears to be blurred when reproduced.

A further disadvantage is that the vibrations cause the bearing and other components of a drive module of the x-ray anode to be exposed to high loads. These mechanical loads are intensified further by the high operating temperatures of the x-ray tube, so that an increased and premature wear of individual components finally results.

The mechanical instability caused by the vibrations in the anode drive housing may result in a higher noise level, which in the case of a patient to be examined, may result in increased unrest, and in the case of an operator of the x-ray facility, may result in increased distraction.

JP 2005-027914 A discloses an x-ray device having a C-arm, in which a vibration sensor and a vibration compensator are arranged on the x-ray detector. The vibration sensor measures the vibration transmitted to the x-ray detector. The measuring results are used to actuate the vibration compensator such that the vibration compensator neutralizes the vibrations.

DE 60131278T2 describes an anode drive module having a rotating anode plate for use in an x-ray tube. The anode drive module includes a rotor that is connected to the rotatable anode plate via a shaft section. The shaft section includes a material with a first thermal expansion coefficient. The anode drive module includes a bearing shaft that is held rotatably by a bearing surface. The bearing shaft includes a material with a second thermal expansion coefficient. A boss that connects the bearing shaft to the rotor is made of a material with a thermal expansion coefficient that lies between the first and the second thermal expansion coefficients. As a result, the appearance of unequal thermal expansion rates between the components is reduced. As a result, mechanical instabilities are reduced in the drive module, thereby providing a high image quality of the x-ray image produced.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved C-arm x-ray device having a C-arm and an x-ray source and an x-ray detector arranged on the C-arm for producing image recordings with a high image quality, and an associated method are provided.

A C-arm x-ray device includes a C-arm and an x-ray source and an x-ray detector arranged on the C-arm. At least one damping element with an oscillation-damping effect is arranged between the x-ray source and the C-arm, by which transmission of oscillations from the x-ray source to the C-arm may be reduced. The C-arm x-ray device also includes at least one holding element arranged on the C-arm, by which the oscillation-damping effect of the damping element may be influenced. The advantage is that the oscillations generated by the x-ray source and transmitted to the x-ray detector may be influenced via the C-arm, thereby improving the quality of the x-ray images produced. The term C-arm x-ray device may include both stationary and also mobile C-arm x-ray devices.

In an embodiment, the oscillation-damping effect of the damping element may be reduced or eliminated.

The damping element may include at least one damping device made of rubber and/or a spring device. By using this, the damping element may dispense with a high oscillation-damping effect and may also be produced in a cost-effective manner.

In another embodiment, the holding element in a first position may permit the oscillation-damping effect of the damping element and in a second position may reduce or eliminate the oscillation-damping effect of the damping element. The oscillation-damping effect of the damping element may be switched off (e.g., for the time period involving moving the x-ray source along the C-arm and during the idling of the x-ray source to readmit the oscillation-damping effect of the damping element).

In one embodiment, the damping element and the holding element may form one unit. A space-saving variant may thus be produced.

The holding element may include an electromagnetically excitable holding device, by which the oscillation-damping property of the damping element may be influenced. An electromagnetic control of the holding element may as a result be provided.

In one embodiment, a method having a C-arm x-ray device is provided. The oscillation-damping property of the damping element may only be influenced by the holding element when the x-ray source is moved along the C-arm.

DETAILED DESCRIPTION OF THE DRAWINGS

Figure 1:
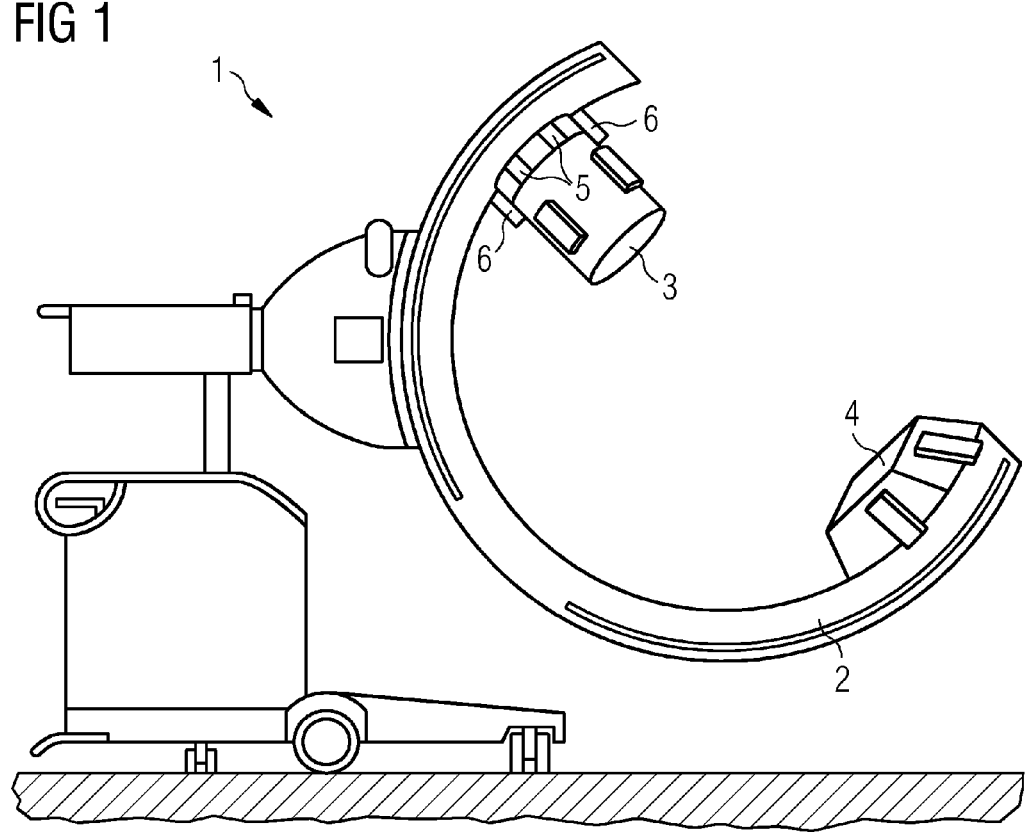
FIG. 1 shows a basic schematic of one embodiment of a C-arm x-ray device having damping element and a holding element.

FIG. 1 shows a basic schematic of one embodiment of a C-arm x-ray device having a damping element and a holding element. A movable C-arm x-ray device 1 includes a C-arm 2 and an x-ray source 3 arranged on the C-arm 2 and an x-ray detector 4 arranged on the C-arm 2. Two damping elements 5 with an oscillation-damping effect are arranged between the x-ray source 3 and the C-arm 2. The damping element 5 reduces transmission of oscillations of the x-ray source 3, which are caused by a high rotational speed of a rotary diode (not shown) arranged in the x-ray source 3, onto the C-arm 2 and thus also onto the x-ray detector 4. In addition, the damping elements 5 reduce transmission of noises that are generated, for example, by an oil pump (not shown) arranged in the x-ray source 3, onto the C-arm 2.

The C-arm x-ray device 1 further includes two holding elements 6 arranged on the C-arm 2. The holding elements 6 allow the oscillation-damping effect of the damping elements 5 to be influenced by the oscillation-dampening effect of the damping elements 5 being permitted or eliminated, for example. The holding elements 6 thus allow for a targeted control of the damping that may be dispensed with by the damping elements 5. The damping elements 5 may include a rubber and or spring device (not shown). The transmission of vibrations from the x-ray source 3 onto the C-arm 2 may be prevented if the rubber device is very soft and the x-ray source 3 is not moved along the C-arm 2, for example, in order to produce 3-dimensional recordings, but is instead in the idle state. On account of the inadequate fixing of the x-ray source 3 to the C-arm 2, during a movement of the x-ray source 3 along the C-arm 2, this leads to instability and a worsened position orientation of the x-ray source 3 and consequently results in an impairment of the quality of the x-ray images produced during the movement of the x-ray source 3. In accordance with one or more of the present embodiments, the oscillation-damping effect of the damping elements 5 is therefore switched off by the fastening elements 6 during the movement times of the x-ray source 3 along the C-arm 2.

Figure 2:
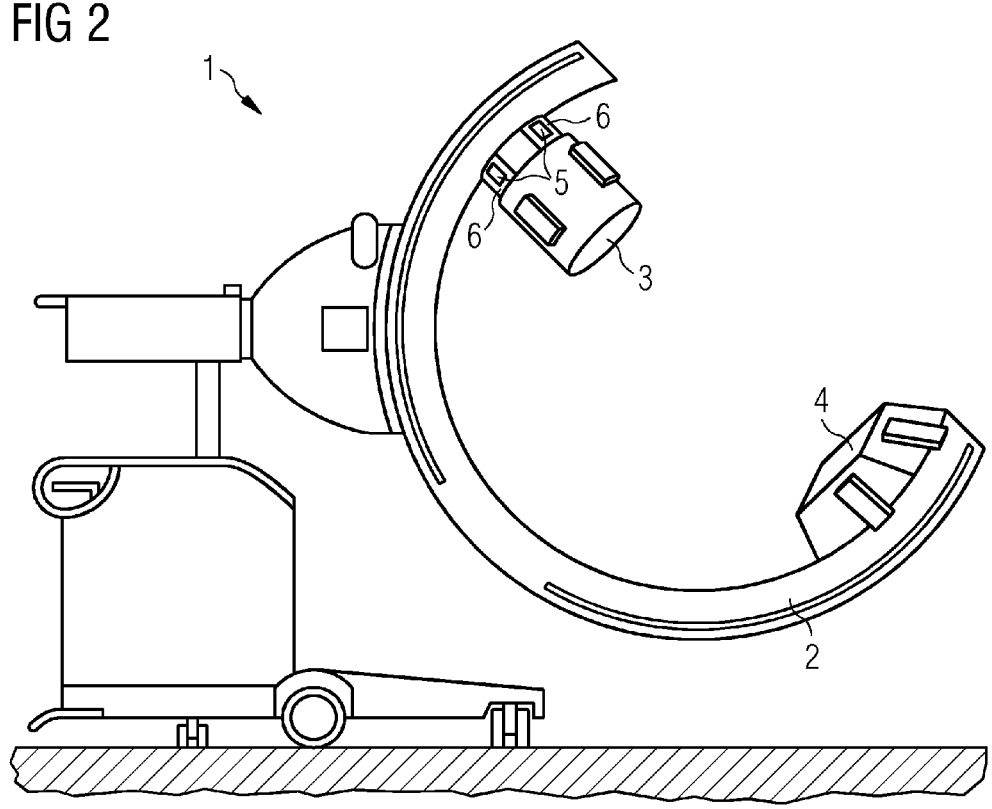
FIG. 2 shows a basic schematic of one embodiment of a C-arm x-ray device having an arrangement, in which the damping element and the holding element form a unit.

FIG. 2 shows a basic schematic of one embodiment of a C-arm x-ray device having an arrangement, in which the damping element and the holding element form a unit. A moveable C-arm x-ray device 1 includes a C-arm 2, an x-ray source 3 arranged on the C-arm 2, and an x-ray detector 4 arranged on the C-arm 2. Two arrangements are attached between the C-arm 2 and the x-ray source 3, in which a damping element 5 and a holding element 6 form a unit in each instance. The damping element 5 and the holding element 6 enable the transmission of oscillations from the x-ray source 3 onto the C-arm 2 to be permitted, reduced or switched off.

Figure 3A:
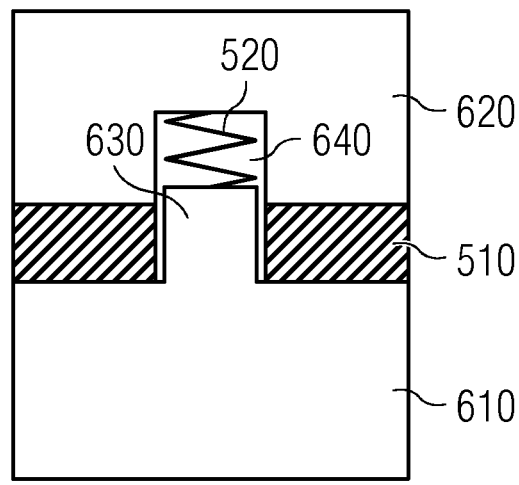
FIG. 3a shows a cross-section of one embodiment of an arrangement, in which a damping element and a holding element form a unit, and the oscillation-damping effect of the damping element is activated.

FIG. 3a shows a cross-section of one embodiment of an arrangement, in which a damping element and a holding element form a unit, and the oscillation-damping effect of the damping element is activated. The arrangement includes a damping element including a rubber device 510 and a spring device 520. The arrangement includes a holding element having a first part 610 that is attached to a C-arm (not shown), and a second part 620 that is fastened to an x-ray source (not shown). The first part 610 and the second part 620 of the holding element are embodied to be square. A cylindrical bolt 630 is fixedly arranged centrally on a topside of the first part 610. The spring device 520 is attached to a topside of the cylindrical bolt 630. A cylindrical recess 640 is incorporated centrally on the lower side of the second part 620. The recess 640 is embodied such that the recess 640 may receive the bolt 630 and the unstressed spring device 520. The spring device 520 may optionally also be fastened to the surface of the second part 620 bordering the topside of the recess 640. The rubber device 510 is arranged between the first part 610 and the second part 620 of the holding element and includes, centrally, a hole in the size of the recess 640.

The first part 610 and the second part 620 of the holding element are surrounded in each instance by an electromagnetically excitable holding device (e.g., an electromagnetically excitable winding) that is not shown in each instance. The two windings are embodied such that when electrical voltages are applied to the windings, a magnetic field, by which the first part 610 and the second part 620 of the holding element attract each other mutually, is produced. As a result, the rubber device 510 and the spring device 520 are pressed together. When voltages are not applied, and a magnetic field is not produced, the holding element is in a first position, in which vibrations that are generated by the x-ray source during a normal operating stage are attenuated by the rubber device 510 and the spring device 520. As a result, a transmission of the oscillations onto the C-arm and thus also onto an x-ray detector (not shown) arranged on the C-arm is prevented, thereby increasing the quality of the x-ray recordings produced.

Figure 3B:
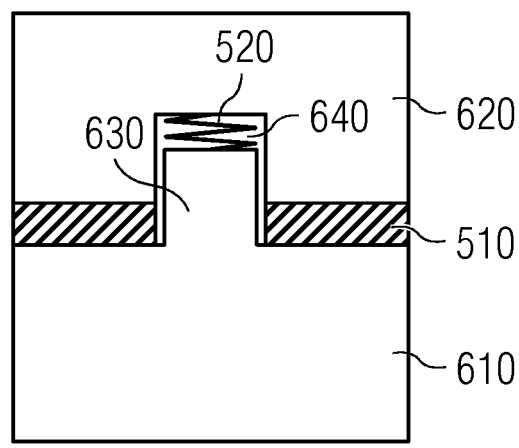
FIG. 3b shows a cross-section of one embodiment of an arrangement, in which a damping element and a holding element form a unit, and the oscillation-damping effect of the damping element is switched off.

FIG. 3b shows a cross-section of one embodiment of an arrangement, in which a damping element and a holding element form a unit, and the oscillation-damping effect of the damping element is switched off. The structure of the damping element and of the holding element corresponds to the structure described in FIG. 3a. The oscillation-damping effect of the damping element is switched off in that voltages are applied to the electromagnetic excitable windings (not shown), and a magnetic field, by which the first part 610 and the second part 620 of the holding element are mutually attracted, is as a result generated. As a result, the rubber device 510 and the spring device 520 are pressed together. The holding element is now in a second position. In the pressed state, the rubber device 510 and the spring device 520 lose their oscillation-damping effect, as a result of which vibrations caused by the x-ray source are consequently no longer eliminated. If the supply of voltages to the electromagnetically excitable windings is interrupted, the return forces produced when pressing the rubber device 510 and the spring device 520 together cause the first part 610 and the second part 620 of the holding element to move apart from one another and the initial state to be produced before applying the electrical voltages, in which the rubber device 510 and the spring device 520 again develop the oscillation-damping effect.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A C-arm x-ray device comprising:
   a C-arm;
   an x-ray source arranged on the C-arm;

an x-ray detector arranged on the C-arm;

at least one damping element with an oscillation-damping effect arranged between the x-ray source and the C-arm, transmission of oscillations from the x-ray source to the C-arm being reducible with the at least one damping element; and at least one holding element arranged on the C-arm, the oscillation-damping effect of the at least one damping element being influenceable with the at least one holding element.

2. The C-arm x-ray device as claimed in claim 1, wherein the oscillation-damping effect of the at least one damping element is reducible or eliminatable.

3. The C-arm x-ray device as claimed in claim 1, wherein the at least one damping element includes at least one damping device made of rubber, a spring device, or the at least one damping device made of rubber and the spring device.

4. The C-arm x-ray device as claimed in claim 2, wherein the at least one holding element permits the oscillation-damping effect of the at least one damping element in a first position and reduces or eliminates the oscillation-damping effect of the at least one damping element in a second position.

5. The C-arm x-ray device as claimed in claim 1, wherein the at least one damping element and the at least one holding element form a unit.

6. The C-arm x-ray device as claimed in claim 1, wherein the at least one holding element comprises an electromagnetically excitable holding device, by which an oscillation-damping property of the at least one damping element is influenceable.

7. The C-arm x-ray device as claimed in claim 2, wherein the at least one damping element includes at least one damping device made of rubber, a spring device, or the at least one damping device made of rubber and the spring device.

8. The C-arm x-ray device as claimed in claim 3, wherein the at least one holding element permits the oscillation-damping effect of the at least one damping element in a first position and reduces or eliminates the oscillation-damping effect of the at least one damping element in a second position.

9. The C-arm x-ray device as claimed in claim 2, wherein the at least one damping element and the at least one holding element form a unit.

10. The C-arm x-ray device as claimed in claim 3, wherein the at least one damping element and the at least one holding element form a unit.

11. The C-arm x-ray device as claimed in claim 4, wherein the at least one damping element and the at least one holding element form a unit.

12. The C-arm x-ray device as claimed in claim 2, wherein the at least one holding element comprises an electromagnetically excitable holding device, by which an oscillation-damping property of the at least one damping element is influenceable.

13. The C-arm x-ray device as claimed in claim 3, wherein the at least one holding element comprises an electromagnetically excitable holding device, by which an oscillation-damping property of the at least one damping element is influenceable.

14. The C-arm x-ray device as claimed in claim 4, wherein the at least one holding element comprises an electromagnetically excitable holding device, by which an oscillation-damping property of the at least one damping element is influenceable.

15. The C-arm x-ray device as claimed in claim 5, wherein the at least one holding element comprises an electromagnetically excitable holding device, by which an oscillation-damping property of the at least one damping element is influenceable.

16. A method using a C-arm x-ray device, the C-arm x-ray device comprising a C-arm, an x-ray source arranged on the C-arm, an x-ray detector arranged on the C-arm, at least one damping element with an oscillation-damping effect arranged between the x-ray source and the C-arm, and at least one holding element arranged on the C-arm, transmission of oscillations from the x-ray source to the C-arm being reducible with the at least one damping element, the oscillation-damping effect of the at least one damping element being influenceable with the at least one holding element, the method comprising:

influencing an oscillation-damping property of the at least one damping element only by the at least one holding element when the x-ray source is moved along the C-arm.

* * * * *